United States Patent [19]
Henrick et al.

[11] 3,943,157
[45] Mar. 9, 1976

[54] SYNTHESIS OF CODLING MOTH ATTRACTANT

[75] Inventors: Clive A. Henrick; John B. Siddall, both of Palo Alto, Calif.

[73] Assignee: Zoecon Corporation, Palo Alto, Calif.

[22] Filed: Apr. 1, 1974

[21] Appl. No.: 456,504

Related U.S. Application Data

[63] Continuation-in-part of Ser. No. 164,876, July 26, 1971, Pat. No. 3,818,049.

[52] U.S. Cl..... 260/448.8 R; 260/347.2; 260/345.9; 260/456 R; 260/465.8 R; 260/554; 260/595; 260/601 R; 260/615 R; 260/632 R; 260/635 D; 260/999; 260/456 P
[51] Int. Cl.² .................. C07F 7/04; C07F 7/18
[58] Field of Search .................. 260/448.8 R

[56] References Cited
UNITED STATES PATENTS
2,906,768  9/1959  Haluska ...................... 260/448.8 R
3,742,068  6/1973  Moersch et al. ............. 260/448.8 R X

OTHER PUBLICATIONS
Corey et al., *J.A.C.S.*, 94, p. 6190, (1972).
Eaton et al., *J. Org. Chem.*, 37, p. 1947, (1972).
*J.A.C.S.*, 74, p. 1003, (1952).
*J.A.C.S.*, 74, p. 3024, (1952).

*Primary Examiner*—Paul F. Shaver
*Attorney, Agent, or Firm*—Donald W. Erickson

[57] ABSTRACT

Sterospecific synthesis of an attractant for the codling moth by reacting sorbic aldehyde with an organometallic reagent to yield a 1-ether of trans-8-trans-10-dodecadiene-1,7-diol which is reduced via a 7-sulfonic acid ester to yield an ether of trans-8-trans-10-dodecadiene-1-ol and hydrolyzed to trans-8-trans-10-dodecadien-1-ol.

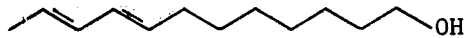

3 Claims, No Drawings

SYNTHESIS OF CODLING MOTH ATTRACTANT

This application is a continuation-in-part of U.S. Ser. No. 164,876, filed July 26, 1971 now U.S. Pat. No. 3,818,049, issued June 18, 1974.

BACKGROUND OF THE INVENTION

The present invention relates to the synthesis of trans-8-trans-10-dodecadien-1-ol, an attractant of the codling moth. This moth, *Carpocapsa pomenella*, is a world-wide pest of apples. The identification of this attractant of the codling moth has been reported in *Chemical ) Engineering News*, 37, Dec. 21, 1970.

It is an object of the present invention to provide a synthesis for the preparation of trans-8-trans-10-dodecadien-1-ol and key intermediates therefor which used readily available starting materials and is economical to practice. The compound can be used as an attractant for the monitoring, through selective trapping, of insect populations. Population counts thus obtained are used in determining the frequency and quantity of spray of insecticide or other insect control agents. The compound can also be used for the direct control of insect populations as by mass trapping. Other objects and advantages will become apparent as the invention is hereinafter described in detail.

SUMMARY OF THE INVENTION

In the practice of the invention, there is first prepared the C-1 ether of trans-8-trans-10-dodecadiene-1,7-diol (III) which may be outlined as follows:

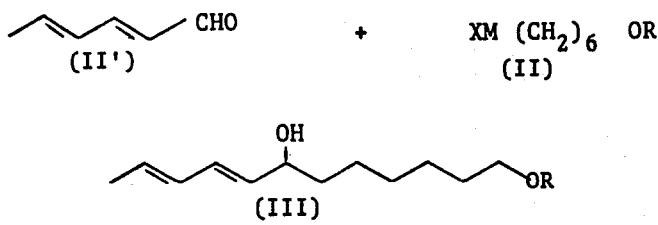

In the above formula, R represents a base stable group such as tetrahydropyran-2-yl, tetrahydrofuran-2-yl, t-butyl, benzyl, trityl, ethoxyethyl ($CH_3$—$CH_2$-O-CH($CH_3$)—), trimethylsilyl, triethylsilyl, triphenylsilyl, diphenylmethylsilyl, tert-butyldimethylsilyl, dimethylisopropylsilyl, and the like protective groups which are conventionally employed in organo-metallic reactions such as Grignard reactions and which are stable under basic reaction conditions. X represents chloro or bromo and M represents a metal such as lithium, magnesium or zinc.

The ether (III), a key intermediate, is prepared in accordance with the present invention by reacting trans sorbic aldehyde (2,4-hexadien-1-al) with an organometallic agent.

As starting materials one may use either 1,6-hexamethylenediol or 6-halohexan-1-ol, both of which are commercially available. If 1,6-hexamethylenediol is used it is selectively halogenated to yield 6-halohexan-1-ol, where the halogen is chlorine or bromine. Selective halogenation may be carried out by heating the alcohol with a concentrated aqueous halogen acid or with a phosphorus trihalide. The reaction with hydrochloric acids catalyzed by the addition of sulfuric acid and may be assisted by the addition of zinc chloride. An organic solvent medium inert to the reaction such as aliphatic or aromatic hydrocarbons and the like, e.g., heptane, pentane, benzene, toluene and the like is used.

The 6-halohexan-1-ol compound is then reacted with a base stable reagent to form a base stable protective group as illustrated in the following equation:

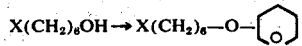

The hydroxyl group of the 6-halohexan-1-ol is protected during the subsequent reaction with an organometallic reagent by a base stable group. Aliphatic alcohols require protective groups of special types which can be later cleaved under mild conditions. Methyl ether derivatives often used with aromatic alcohols are usually not suitable as protective groups for aliphatic alcohols because the more drastic conditions required for cleavage lead to secondary changes. Several types of base stable groups are suitable, viz. ethers such as tetrahydropyran-2-yl, tetrahydrofuran-2-yl, t-butyl, trimethylsilyl, t-butyldimethylsilyl, triethylsilyl, triphenylsilyl, diphenylmethylsilyl, and the like. Tetrahydropyran-2-yl and tetrahydrofuran-2-yl ethers may be prepared by the reaction of the alcohol with dihydropyran and dihydrofuran, respectively, under acid catalysis. This preparation has been reported by Green, et al., *J. Med. Chem.* 10, 533 (1967). The t-butyl ether can be prepared by treating the alcohol with isobutene in the presence of sulfuric acid. These ethers are stable to base, to Grignard reagents, and to oxidation, and the original alcohol can be recovered by gentle acid hydrolysis. The trimethylsilyl, triethylsilyl, and triphenylsilyl ethers may be prepared by the reaction of the alcohol and the corresponding chlorosilane in the presence of a nitrogenous catalyst such as ammonia, triethylamine, and the like. Alternatively, they may be prepared from the alcohol and a corresponding hexahydrocarbondichlorosilazane, such as hexamethyldichlorosilazane, in the presence of a catalytic amount of trihydrocarbonchlorosilane. If ammonia is used as a hydrogen chloride acceptor, an inert solvent, such as benzene, is employed and dry ammonia is passed through the reaction mixture. It is critical and essential that anhydrous conditions be employed since the trialkylsilyl group is readily hydrolyzed.

Alternatively, hexaalkyldisilazane may be added to a cooled 6-halohexan-1-ol while the reaction mixture is kept below about 20°C with trialkylchlorosilane as catalyst. A reaction takes place with the formation of 6-halohexan-1-oxytrialkylsilane and ammonia. The tert-butyldimethylsilyl ethers may be prepared by the reaction of dimethyl-tert-butylchlorosilane and the alcohol in the presence of imidazole and dimethylformamide using the method described by Corey and Venkateswarlu, *J. Am. Chem. Soc.*, 94, 6190 (1972).

The ethoxyethyl ethers may be prepared by the reaction of the alcohol with ethylvinyl ether in the presence of an acid catalyst such as dichloroacetic acid using the method of Eaton et al, *J. Org. Chem.*, 37, 1947 (1972).

In carrying out the reaction where Q is tetrahydrofuranyl or tetrahydropyranyl, the 6-halohexan-1-ol is contacted with dihydrofuran or dihydropyran in the presence of a catalytic amount of a strong acid. Suitable strong acids include hydrochloric acid, p-toluenesulfonic acid, sulfuric acid, methanesulfonic acid, etc. A drop of concentrated acid solution or a crystal of solid acid is generally sufficient although as much as 2 milliliters have been employed in a successful synthesis. A large amount would cause hydrolysis of the heterocyclic ring with resultant decrease in yield and, therefore, should be avoided. The exact amount of the reactants are not critical but a slight excess of dihydrofuran or dihydropyran, generally from 1.1 to 1.5 moles of the heterocyclic compound per mole of halo alcohol is considered satisfactory. The order of addition may also be varied. The preferred methods are hereinafter described.

6-Halohexan-1-oxytrimethylsilane may be prepared by the addition of an equimolar amount of the alcohol in anhydrous benzene to cooled trimethylchlorosilane while stirring and passing gaseous ammonia therethrough until the odor of ammonia persists. The ammonium chloride by-product may be filtered off and the filtrate distilled to recover first the solvent and then the 6-halohexan-1-oxytrimethylsilane.

Further modifications for the preparation of trialkylsilyl derivatives of hydroxy compounds which are adaptable to the present process may be seen in *J. Am. Chem. Soc.*, 74, 1003 (1952) and *J. Am. Chem. Soc.*, 74, 3024 (1952).

The organo-metallic reagent (II) is prepared from 2-[(6-halohexyl)oxy] tetrahydropyran or other suitable protective ethers by reaction with a reasonably active metal such as lithium, magnesium or zinc. Magnesium, the preferred metal, may either be in the form of thin turnings or granules. The reaction takes place in an anhydrous ethereal solution. The ethereal solution must be absolutely dry as a trace of water may prevent the reaction from starting. Suitable ethers include both linear and cyclic ethers such as diethyl ether, di-n-butyl ether, tetrahydrofuran, and the like.

The reaction of sorbic aldehyde (II') with the organometallic reagent (II) occurs vigorously. The organo-metallic reagent is kept under an inert atmosphere such as nitrogen, helium, argon or the like and is cooled to about 0°C. A solution of sorbic aldehyde in an organic solvent medium inert to the reaction is added dropwise at such a rate that refluxing is kept under control or preferably cooling in an ice-bath to maintain temperature about 0° C. Suitable solvents include both linear and cyclic ethers such as diethyl ether, tetrahydrofuran, and the like, hydrocarbons such as pentane, hexane, heptane and the like, and methylene chloride. After the sorbic aldehyde solution has been added, the reaction mixture is stirred for several hours at about room temperature.

The organo-metallic complex formed by the reaction of sorbic aldehyde (II') and the organo-metallic reagent (II) is decomposed under neutral or basic conditions such as by the addition of a saturated ammonium chloride solution to yield the alcohol-ether (III). Hydrolysis of the organo-metallic complex with saturated ammonium chloride solution possesses the advantage that the resulting solution of the alcohol is almost neutral. This is important in the instant synthesis since the presence of acid could dehydrate the 7-alcohol or prematurely hydrolyze the base stable protecting group. As the reaction of the organo-metallic complex with saturated ammonium chloride solution may be exothermic it is desirable to cool the reaction mixture to room temperature or lower and add the saturated ammonium chloride solution slowly with stirring. The reaction product (III), a trans-8-trans-10-dodecadien-7-ol ether, is isolated by filtering off the precipitate and removing the solvent from the filtrate under reduced pressure. Decomposition of the organo-metallic complex under neutral or basic conditions can be accomplished using water or a dilute or saturated solution of ammonium salts, sodium salts, potassium salts, and the like, e.g., dilute aqueous ammonium chloride, saturated or dilute aqueous sodium sulfate, dilute aqueous sodium hydroxide, dilute aqueous potassium hydroxide, and the like.

In the practice of the invention there is then prepared the ether (IV) of trans-8-trans-10-dodecadien-1-ol which may be outlined as follows:

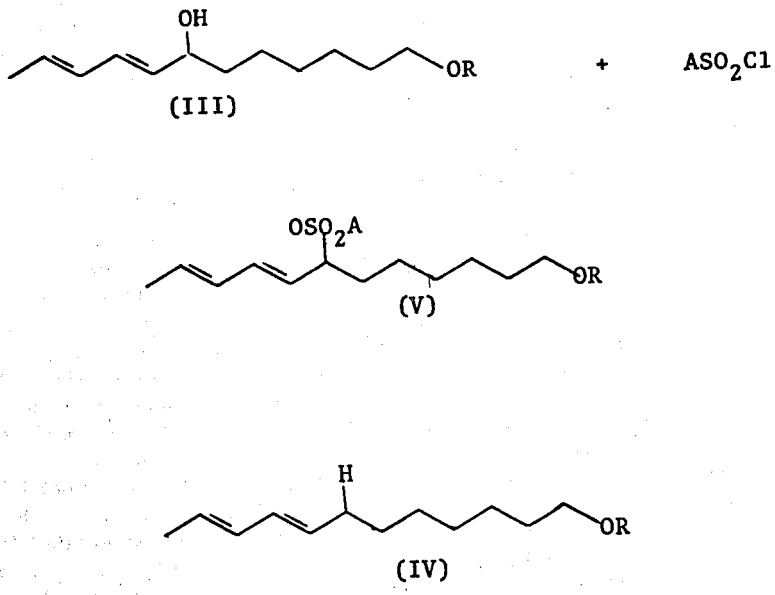

In the above formula, R represents a base stable group and A represents an alkyl or aryl group such as methyl, toluene or a toluene derivative.

The ether (IV), a key intermediate, is prepared in accordance with the present invention by reacting a trans-8-trans-10-dodecadien-7-ol ether with an acid chloride of an alkyl or arylsulfonic acid followed by reduction of the resultant sulfonic acid ester. Suitable acid chlorides include methanesulfonyl chloride (usually identified by the abbreviation mesyl chloride), p-toluenesulfonyl chloride (usually identified by the abbreviation tosyl chloride), p-bromotoluenesulfonyl chloride (usually identified by the abbreviation brosyl chloride), and the like. The sulfonic acid esters thus prepared (V) are usually identified by the abbreviations mesylates, tosylates, brosylates, and the like. A facile synthesis of mesylates has been reported by Crossland, et al., *J. Org. Chem.* 35, 3195 (1970). Although these sulfonic acid esters can be prepared by the reaction of the alcohol with a suitable acid chloride in anhydrous pyridine at room temperature or below, the Crossland et al synthesis is preferred because it avoids possible side reactions between the sulfonic acid esters produced and the solvent, pyridine. The synthesis reported by Crossland et al. deviates from the usual procedure by the use of triethylamine as a base and methylene chloride, pentane or ether as solvent. In the preferred practice of the present invention sulfonic acid esters are prepared using triethylamine as a base and either an ether such as diethyl ether, dipropyl ether, and the like or a hydrocarbon such as pentane, hexane, heptane, and the like, as a solvent.

The sulfonic acid esters (V) formed in the practice of the present invention are very reactive and it is therefore important that the reactants and product be well chilled. The temperature of the ester, in the preferred practice of the invention, should not be above about 5°C. A trans-8-trans-10 -dodecadien-7-ol ether (III) is dissolved in an anhydrous inert solvent chosen from the solvents discussed above under an inert atmosphere such as helium, argon or the like. The solution is cooled to 0° to −78°C and triethylamine is added with stirring. An aliphatic sulfonic acid chloride such as mesyl chloride is added dropwise with stirring. Stirring may be continued for several hours.

Instead of isolating the sulfonic acid ester it is preferable to prepare the ether (IV) by reduction of the sulfonic acid ester (V) in solution. Reduction of the sulfonic acid ester (V) completes the reductive elimination of the hydroxyl group of the secondary alcohol (III). Sodium amalgam is the classical reducing agent, however in the practice of the present invention lithium aluminum hydride or sodium bis(2-methoxyethoxy) aluminum hydride, trimethoxy lithium aluminum hydride, diethyl aluminum hydride, and disobutyl aluminum hydride are preferred. The sulfonic acid ester (V) is maintained at a temperature below 0°C and preferably about −20°C. Mesylates are quite useful as synthetic intermediates in this reaction because the mesylate fragment reduces to methyl mercaptan, which is easily removed. An excess of reducing agent is added dropwise with stirring. After the reducing agent is added, the reaction mixture may be allowed to warm gradually to room temperature with stirring to insure complete reaction. Following complete reduction the reaction mixture is treated with aqueous ammonium chloride to quench any excess reducing agent remaining in the reaction mixture. The product ether (IV) is isolated from the reaction mixture as a colorless oil.

In the final step of the practice of the present invention the ether (IV) is hydrolyzed to remove the base stable protective group denoted R in compounds (II) and (III). As previously discussed, the base stable protective groups can be split under mild conditions. Thus

the attractant of the codling moth (I) can be recovered by using hydrolysing agents and conditions for hydrolysis of the ether (IV) that depend upon the nature of the protecting group but, generally, the mildest possible conditions are desirable to protect the trans, trans stereochemistry. Hydrolyzing agents may be water or dilute aqueous or alcoholic solutions of acids, such as p-toluenesulfonic acid, sulfuric acid, hydrochloric acid, hydrobromic acid, nitric acid, acetic acid, perchloric acid, etc. When the protecting group is a completely organic ether or acetal group, from about 0.2 to about 2.5 moles of acid per mole of ether may be intimately mixed with the ether coupling product in aqueous ethanol or other alcohol or aqueous tetrahydrofuran for from about two to four hours at temperatures ranging from 20° to about 50°C. Under these acidic conditions, it is preferable to employ lower temperatures and larger ratio of acid to water alcohol than to use elevated temperatures and a smaller amount of acid. When the protecting group is a silyl group, such as trimethylsilyl, the protecting group may be removed by merely boiling for several minutes with a small amount of water with sufficient alcohol to give a homogeneous solution as described in *J. Am. Chem. Soc.*, 74, 3024 (1952). In the absence of acid, elevated temperatures may be used.

The tert-butyldimethylsilyl group can be removed by treatment with about 3 equivalents of tetra-n-butylammonium fluoride in tetrahydrofuran using the method of Corey and Venkateswarlu, *J. Am. Chem. Soc*, 94, 6190 (1972).

The following examples are provided to illustrate the present invention. All temperatures are in degrees centigrade.

EXAMPLE 1

To 25 g. Mg turnings add 1 g. of I₂ and heat to activate. After cooling add 750 ml. diethyl ether with stirring.

To the above prepared solution is added 100 g. of 2-[(6′-chlorohexyl)oxy] tetrahydropyran in 125 ml. diethyl ether. Head to gentle reflux and stir vigorously until Gilman Test indicates reaction has started. Add another 100 g. of 2-[(6′-chlorohexyl)oxy] tetrahydropyran in 100 ml. tetrahydrofuran with continued refluxing. Stir overnight at room temperature to yield the Grignard.

EXAMPLE 2

The solution of the Grignard of Example 1 is cooled to 0° under nitrogen. To this solution is added a total of 80 g. all-trans sorbic aldehyde in tetrahydrofuran dropwise with stirring, maintaining the temperature at 0° until the addition is complete. The mixture is allowed to rise to room temperature and stand for about 2 hours. Then 150 ml. of a saturated aqueous ammonium chloride solution is added dropwise with stirring while cooling in an ice-bath. A dense white precipitate forms and settles to the bottom of the reaction vessel. The reaction mixture is decanted and precipitate washed with ether. The filtrate is washed with saturated aqueous sodium bicarbonate and dried with calcium sulfate, filtered and the solvent is removed under reduced pressure to yield 1-(tetrahydropyran-2'-yloxy)-trans-8-trans-10-dodecadien-7-ol.

EXAMPLE 3

To a solution of 2 g. of ether of Example 2 in 15 ml. absolute diethyl ether under an argon atmosphere cooooled to −20°, add 1.2 ml. triethylamine with stirring. Stir and add 0.60 ml. mesyl chloride dropwise at −20°. Allow the reaction mixture to stand at −20° for 2 hours to yield the 7 mesylate (V).

EXAMPLE 4

To the above solution of the 7-mesylate (V) of Example 3, at −20° is added 2 ml. of LiAlH$_4$ in ether (Foote, 3.9M). Allow the reaction mixture to rise to room temperature and stir overnight. Add 2 ml. H$_2$O dropwise (care should be taken as hydrogen is evolved) and pour the reaction mixture into an aqueous ammonium chloride solution. Extract with diethyl ether and wash with H$_2$O and NaCl. Dry with CaSo$_4$ to yield 1-(tetrahydropyran-2'-yloxy)-trans-8-trans-10-dodecadiene (IV), a colorless oil with an odor of methyl mercaptan, which is purified by thin layer or column chromatography (50% ether/hexane) or distillation.

EXAMPLE 5

One gram of the ether (IV) of Example 4 is refluxed with 50 ml. methanol, 10 ml. water and 0.3 g. p-toluenesulfonic acid for 1 hour. Most of the methanol is removed under reduced pressure. The reaction mixture is extracted with diethyl ether and washed with water and brine and dried with calcium sulfate to yield trans-8-trans-10-dodecadien-1-ol (I), an oil, which can be purified by distillation, or crystallization at low temperature.

EXAMPLE 6

To a solution of 127.19 g. of 1-(tetrahydropyran-2'-yloxy)-trans-8-trans-10-dodecadien-7-ol in 450 ml. absolute diethyl ether under a nitrogen atmosphere cooled to −50° add 72.1 ml. of triethylamine with stirring. Stir and add 37.2 ml. mesyl chloride at −47°. Allow the reaction mixture to warm to −18° to yield the respective 7-mesylate.

EXAMPLE 7

To a solution of the 7-mesylate of Example 6 at −40° is added dropwise 127 ml. of LiAlH$_4$ (3.9M) in ether. Allow the reaction mixture to rise to room temperature and stir overnight. To the reaction mixture add 70 ml. of aqueous ammonium chloride solution, taking care as hydrogen is intitally evolved. Then 500 ml. dry diethyl ether is added and mixture refluxed gently for one-half hour. A granular white precipitate forms which is separated and washed with diethyl ether. The filtrate is dried with calcium sulfate and concentrated under reduced pressure to yield 1-(tetrahydropyran-2'-yloxy)-trans-8-trans-10-dodecadiene.

EXAMPLE 8

117 G. of the ether of Example 7 is refluxed with 500 ml. ethanol, 50 ml. water and 15 g. of p-toluenesulfonic acid for 3 hours to yield (I) which is worked up as in Example 5.

EXAMPLE 9

13.8 G. of trimethylchlorosilane and 11.4 g. of 6-bromohexan-1-ol are mixed together in 100 ml. of dry benzene and are stirred in an ice-bath while anhydrous ammonia is passed therethrough until the odor of ammonia persists to obtain 6-bromohexyloxytrimethylsilane, which is worked up by filtration, followed by evaporation of the filtrate and distillation in vacuo.

EXAMPLE 10

To 33 g. of dimethyl-tert-butylchlorosilane in 100 ml. of dimethylformamide is added 27 g. of 6-chlorohexan-1-ol and 340 g. of imidazole. The reaction mixture is allowed to stand at room temperature for 3 days to yield 6-chlorohexyloxy-dimethyl-tert-butylsilane, which is worked up by pouring into water, extracting with ether, washing with water, drying over calcium sulfate, removing the solvent by evaporation and purifying by distillation.

EXAMPLE 11

Following the procedure of Example 1, the Grignard of 30 g. of 6-chlorohexyloxydimethyl-tert-butyl silane is prepared.

A solution of this Grignard is cooled to 0° under nitrogen and 20 g. of all trans sorbic aldehyde in tetrahydrofuran is added dropwise, with stirring, while the temperature is maintained at 0°. The reaction mixture is allowed to warm to room temperature. After standing for 3 hours, 40 ml. of saturated aqueous ammonium chloride is added dropwise with stirring while cooling in an ice-bath. The reaction mixture is worked up following the procedure of Example 2 to yield 1-(dimethyl-tert-butylsilyloxy)-trans-8, trans-10-dodecadien-7-ol.

EXAMPLE 12

To a solution of 3 g. of the ether of Example 11 in 30 ml. anhydrous pentane under an argon atmosphere cooled to −10° is added 1.5 ml. of triethylamine with stirring, follwoed by the dropwise addition of 1.5 g. of mesyl chloride while the temperature is maintained at −10°. Standing for 4 hours yield the 7-mesylate (V).

To this solution, there is added 4 ml. of Red-al$^R$ (70% solution of sodium bis(2-methoxyethoxy)aluminum hydride in benzene) at −10°. The reaction mixture is allowed to warm to room temperature and is stirred overnight. Water (3ml.) is added dropwise and the reaction mixture is worked up following the procedure of Example 4 to yield 1-(dimethyl-tert-butylsilyloxy) trans-8,trans-10-dodecadiene (IV), which is purified by distillation.

EXAMPLE 13

To a solution of 1 g. of the ether (IV) of Example 12 in 50 ml. tetrahydrofuran at room temperature ia added 1.5 g. of tetra-n-butylammonium fluoride. The reaction mixture is allowed to stand for 1 hour to yield trans-8,trans-10 dodecadien-1-ol, which is worked up by pouring into saturated aqueous ammonium chloride, extracting with ether, washing with water, drying over calcium sulfate, removing the solvent by evaporation and purifying by recrystallization.

It is understood that various other modifications will be apparent to and can readily be made by those skilled in the art without departing from the scope and spirit of this invention. Accordingly, it is not intended that the scope of the claims appended hereto be limited to the description set forth herein but rather that the claims be construed as encompassing all the features of patentable novelty which reside in the present invention including all features which would be treated as equivalents thereof by those skilled in the art to which the invention pertains.

What is claimed is:

1. A compound of the following formula:

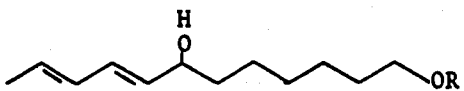

wherein R is trimethylsilyl, t-butyldimethylsilyl, triethylsilyl, triphenylsilyl, diphenylmethylsily, or dimethylisopropylsilyl, said compound having a trans-8,trans-10-isomeric configuration.

2. A compound according to claim 1 wherein R is trimethylsilyl or t-butyldimethylsilyl.

3. The compound according to claim 2 wherein R is trimethylsilyl.

* * * * *